(12) United States Patent
Couture et al.

(10) Patent No.: US 10,543,100 B2
(45) Date of Patent: Jan. 28, 2020

(54) GLENOID IMPLANT SURGERY USING PATIENT SPECIFIC INSTRUMENTATION

(71) Applicant: ORTHOSOFT, INC., Montreal (CA)

(72) Inventors: Pierre Couture, Montreal (CA); Jean-Sebastien Merette, Montreal (CA); Alain Richard, Lachine (CA); Jean-Guillaume Abiven, Montreal (CA); Thomas Gourgon, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 701 days.

(21) Appl. No.: 14/386,620

(22) PCT Filed: Mar. 28, 2013

(86) PCT No.: PCT/CA2013/050253
§ 371 (c)(1),
(2) Date: Sep. 19, 2014

(87) PCT Pub. No.: WO2013/142998
PCT Pub. Date: Oct. 3, 2013

(65) Prior Publication Data
US 2015/0073424 A1      Mar. 12, 2015

Related U.S. Application Data

(60) Provisional application No. 61/616,623, filed on Mar. 28, 2012, provisional application No. 61/659,272,
(Continued)

(51) Int. Cl.
*A61B 17/17*     (2006.01)
*A61F 2/40*      (2006.01)
(Continued)

(52) U.S. Cl.
CPC ........ *A61F 2/4081* (2013.01); *A61B 17/1684* (2013.01); *A61B 17/1778* (2016.11);
(Continued)

(58) Field of Classification Search
CPC ............ A61B 17/1684; A61B 17/1778; A61B 2017/568; A61B 17/17; A61F 2002/30736; A61F 2002/4085; A61F 2002/4081
(Continued)

(56) References Cited

U.S. PATENT DOCUMENTS

| 4,841,975 A | 6/1989 | Woolson |
| 5,030,219 A | 7/1991 | Matsen, III et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.
(Continued)

*Primary Examiner* — Kevin T Truong
*Assistant Examiner* — Jessica Weiss
(74) *Attorney, Agent, or Firm* — Norton Rose Fulbright Canada LLP

(57) ABSTRACT

A pin placement instrument for placing a pin in a bone comprises an anatomical interface with a hook-like portion being opened in a lateral direction of the instrument to receive a bone therein in a planned position. A drill guide is connected to the anatomical interface and defining at least one guide slot in a longitudinal direction of the instrument.
(Continued)

The guide slot has a lateral opening over its full length in the drill guide to allow lateral withdrawal of the instrument in said lateral direction with the pin placed in the bone passing through the lateral opening. A bushing is removably placed in said guide slot via said longitudinal direction in a planned fit, the bushing defining a throughbore aligned with the guide slot and adapted to receive the pin extending in said longitudinal direction when the bushing is in the guide slot for pin placement.

27 Claims, 16 Drawing Sheets

Related U.S. Application Data filed on Jun. 13, 2012, provisional application No. 61/675,955, filed on Jul. 26, 2012.

(51) Int. Cl.
 *A61B 17/16* (2006.01)
 *A61F 2/30* (2006.01)
 *A61B 17/56* (2006.01)

(52) U.S. Cl.
 CPC .............. *A61B 2017/568* (2013.01); *A61F 2002/30736* (2013.01); *A61F 2002/4085* (2013.01)

(58) Field of Classification Search
 USPC ...................................................... 606/96–98
 See application file for complete search history.

(56) References Cited

U.S. PATENT DOCUMENTS

| | | | |
|---|---|---|---|
| 5,098,383 | A | 3/1992 | Hemmy et al. |
| 5,354,300 | A | 10/1994 | Goble et al. |
| 5,490,854 | A | 2/1996 | Fisher et al. |
| 5,768,134 | A | 6/1998 | Swaelens et al. |
| 5,769,856 | A | 6/1998 | Dong |
| 5,871,018 | A | 2/1999 | Delp et al. |
| 5,916,219 | A | 6/1999 | Matsuno et al. |
| 6,379,386 | B1 | 4/2002 | Resch et al. |
| 6,428,541 | B1 | 8/2002 | Boyd et al. |
| 7,357,057 | B2 | 4/2008 | Chiang |
| 7,468,075 | B2 | 12/2008 | Lang et al. |
| 7,510,557 | B1 | 3/2009 | Bonutti |
| 7,534,263 | B2 | 5/2009 | Burdulis |
| 7,618,451 | B2 | 11/2009 | Berez et al. |
| 7,634,119 | B2 | 12/2009 | Tsougarakis et al. |
| 7,717,956 | B2 | 5/2010 | Lang |
| 7,796,791 | B2 | 9/2010 | Tsougarakis et al. |
| 7,799,077 | B2 | 9/2010 | Lang et al. |
| 7,806,896 | B1 | 10/2010 | Bonutti |
| 7,806,897 | B1 | 10/2010 | Bonutti |
| 7,967,868 | B2 | 6/2011 | White et al. |
| 7,981,158 | B2 | 7/2011 | Fitz et al. |
| 8,062,302 | B2 | 11/2011 | Lang et al. |
| 8,066,708 | B2 | 11/2011 | Lang et al. |
| 8,070,752 | B2 | 12/2011 | Metzger et al. |
| 8,077,950 | B2 | 12/2011 | Tsougarakis et al. |
| 8,083,745 | B2 | 12/2011 | Lang et al. |
| 8,092,465 | B2 | 1/2012 | Metzger et al. |
| 8,094,900 | B2 | 1/2012 | Steines et al. |
| 8,105,330 | B2 | 1/2012 | Fitz et al. |
| 8,122,582 | B2 | 2/2012 | Burdulis, Jr. et al. |
| 8,133,234 | B2 | 3/2012 | Meridew et al. |
| 8,160,345 | B2 | 4/2012 | Pavlovskaia et al. |
| 8,175,683 | B2 | 5/2012 | Roose |
| 8,221,430 | B2 | 7/2012 | Park et al. |
| 8,234,097 | B2 | 7/2012 | Steines et al. |
| 8,241,293 | B2 | 8/2012 | Stone et al. |
| 8,282,646 | B2 | 10/2012 | Schoenefeld et al. |
| 8,298,237 | B2 | 10/2012 | Schoenefeld |
| 8,337,501 | B2 | 12/2012 | Fitz et al. |
| 8,337,507 | B2 | 12/2012 | Lang et al. |
| 8,343,218 | B2 | 1/2013 | Lang et al. |
| 8,366,771 | B2 | 2/2013 | Burdulis et al. |
| 8,377,129 | B2 | 2/2013 | Fitz et al. |
| 8,439,926 | B2 | 5/2013 | Bojarski et al. |
| 8,460,304 | B2 | 6/2013 | Fitz et al. |
| 8,480,754 | B2 | 7/2013 | Bojarski et al. |
| 8,500,740 | B2 | 8/2013 | Bojarski et al. |
| 8,529,568 | B2 | 9/2013 | Bouadi |
| 8,529,630 | B2 | 9/2013 | Bojarski |
| 8,585,708 | B2 | 9/2013 | Fitz et al. |
| 8,545,569 | B2 | 10/2013 | Fitz et al. |
| 8,551,099 | B2 | 10/2013 | Lang |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 | 10/2013 | Bojarski et al. |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,617,172 | B2 | 12/2013 | Fitz et al. |
| 8,617,242 | B2 | 12/2013 | Philipp |
| 8,623,026 | B2 | 1/2014 | Wong et al. |
| 8,634,617 | B2 | 1/2014 | Tsougarakis et al. |
| 8,638,998 | B2 | 1/2014 | Steines et al. |
| 8,641,716 | B2 | 2/2014 | Fitz et al. |
| 8,657,827 | B2 | 2/2014 | Fitz et al. |
| 8,682,052 | B2 | 3/2014 | Fitz et al. |
| 9,289,221 | B2 | 3/2016 | Gelaude et al. |
| 9,381,026 | B2 * | 7/2016 | Trouilloud ......... A61B 17/1739 |
| 9,421,021 | B2 | 8/2016 | Keppler |
| 9,579,106 | B2 * | 2/2017 | Lo ............................ A61B 17/15 |
| 9,936,962 | B2 * | 4/2018 | Heilman ............ A61B 17/1739 |
| 2003/0055502 | A1 | 3/2003 | Lang et al. |
| 2003/0216669 | A1 | 11/2003 | Lang et al. |
| 2004/0133276 | A1 | 7/2004 | Lang et al. |
| 2004/0138754 | A1 | 7/2004 | Lang et al. |
| 2004/0147927 | A1 | 7/2004 | Tsougarakis et al. |
| 2004/0153079 | A1 | 8/2004 | Tsougarakis et al. |
| 2004/0204644 | A1 | 10/2004 | Tsougarakis et al. |
| 2004/0204760 | A1 | 10/2004 | Fitz et al. |
| 2004/0236424 | A1 | 11/2004 | Berez et al. |
| 2005/0234461 | A1 | 10/2005 | Burdulis et al. |
| 2005/0267584 | A1 | 12/2005 | Burdulis et al. |
| 2006/0079963 | A1 | 4/2006 | Hansen |
| 2006/0111722 | A1 | 5/2006 | Bouadi |
| 2007/0083266 | A1 | 4/2007 | Lang |
| 2007/0100462 | A1 | 5/2007 | Lang et al. |
| 2007/0156171 | A1 | 7/2007 | Lang et al. |
| 2007/0157783 | A1 | 7/2007 | Chiang |
| 2007/0198022 | A1 | 8/2007 | Lang et al. |
| 2007/0226986 | A1 | 10/2007 | Park et al. |
| 2007/0233141 | A1 | 10/2007 | Park et al. |
| 2007/0233269 | A1 | 10/2007 | Steines et al. |
| 2007/0250169 | A1 | 10/2007 | Lang |
| 2007/0288030 | A1 * | 12/2007 | Metzger ............... A61B 17/154 606/87 |
| 2008/0114370 | A1 | 5/2008 | Schoenefeld |
| 2008/0147072 | A1 | 6/2008 | Park et al. |
| 2008/0161815 | A1 | 7/2008 | Schoenefeld et al. |
| 2008/0195216 | A1 | 8/2008 | Philipp |
| 2008/0243127 | A1 | 10/2008 | Lang et al. |
| 2008/0262624 | A1 | 10/2008 | White et al. |
| 2008/0275452 | A1 | 11/2008 | Lang et al. |
| 2008/0281328 | A1 | 11/2008 | Lang et al. |
| 2008/0281329 | A1 | 11/2008 | Fitz et al. |
| 2008/0281426 | A1 | 11/2008 | Fitz et al. |
| 2008/0287954 | A1 | 11/2008 | Kunz et al. |
| 2009/0024131 | A1 | 1/2009 | Metzgu et al. |
| 2009/0088753 | A1 | 4/2009 | Aram et al. |
| 2009/0088754 | A1 | 4/2009 | Aker et al. |
| 2009/0088755 | A1 | 4/2009 | Aker et al. |

(56) References Cited

U.S. PATENT DOCUMENTS

| | | |
|---|---|---|
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1* | 4/2009 | Zajac .................. A61B 17/155 606/79 |
| 2009/0110498 A1 | 4/2009 | Park et al. |
| 2009/0118768 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0312249 A1 | 12/2010 | Sanders |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0152869 A1 | 6/2011 | Ek et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0143267 A1* | 6/2012 | Iannotti .............. A61B 17/1746 606/86 R |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |

(56) References Cited

U.S. PATENT DOCUMENTS

| | | |
|---|---|---|
| 2012/0239042 A1 | 9/2012 | Lappin et al. |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110116 A1* | 5/2013 | Kehres ............... A61B 17/1739 606/96 |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2014/0142578 A1* | 5/2014 | Hananouchi ....... A61B 17/1746 606/87 |
| 2015/0265292 A1* | 9/2015 | Olson .................. A61B 17/1684 606/80 |
| 2016/0030196 A1* | 2/2016 | Eraly .................. A61F 2/4612 606/96 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 201227321 Y | 4/2009 |
| CN | 101442960 A | 5/2009 |
| CN | 100502808 C | 6/2009 |
| CN | 201453365 U | 5/2010 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |

(56) References Cited

FOREIGN PATENT DOCUMENTS

| | | |
|---|---|---|
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| EP | 2670314 B1 | 8/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 99/52453 | 10/1999 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2009001083 A1 | 12/2008 |
| WO | 2007041375 A3 | 4/2009 |
| WO | 2008157412 A3 | 4/2009 |
| WO | 2009/058960 A1 | 5/2009 |
| WO | 2009111626 A2 | 9/2009 |
| WO | 2009111639 A1 | 9/2009 |
| WO | 2009111656 A1 | 9/2009 |
| WO | 2009129067 A1 | 10/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2010/150223 A1 | 12/2010 |
| WO | 2011028624 A1 | 3/2011 |
| WO | 2011056995 A2 | 5/2011 |
| WO | 2011060536 A1 | 5/2011 |
| WO | 2011072235 A2 | 6/2011 |
| WO | 2011075697 A2 | 6/2011 |
| WO | 2011056995 A3 | 9/2011 |
| WO | 2011110374 A1 | 9/2011 |
| WO | 2011075697 A3 | 10/2011 |
| WO | 2011072235 A3 | 12/2011 |
| WO | 2012024281 A2 | 2/2012 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

\* cited by examiner

GLENOID IMPLANT SURGERY USING PATIENT SPECIFIC INSTRUMENTATION

FIELD OF THE APPLICATION

The present application relates to shoulder replacement, more specifically to glenoid implant shoulder surgery for instance in total shoulder replacement, and to patient specific instrumentation (PSI) used therefore.

BACKGROUND OF THE ART

The use of implants in shoulder surgery is well-known. In such shoulder surgery, implant components are installed on the glenoid portion of the scapula (i.e., shoulder blade) and/or on the humerus, to replicate the shoulder joint. When an implant is installed on the scapula, it is commonly installed in the glenoid cavity, also known as the glenoid or glenoid fossa. The glenoid is a cavity that receives the head of the humerus in an anatomical shoulder. When an implant is used with the glenoid, the base of the implant is located within the glenoid, and could be secured thereto by fasteners such as screws, or using cement and/or fixation peg or keel.

One of the challenges when installing an implant in the glenoid relates to the positioning of implant. Due to the presence of ligaments and like soft tissue, the positioning of the implant must be planned to replicate as much as possible the normal bio-mechanical movements of the humerus relative to the scapula. Another challenge relates to the positioning of the fasteners that secure the implant to the scapula. Indeed, the scapula is relatively thin, and is surrounded by soft tissue. In order for the implant to be solidly secured to the scapula, the screws must be deep enough within the bone material. However, unless desired by the surgeon, the screws must not pierce through the bone surface so as not to damage soft tissue, such as nerves ligaments, tendons, etc.

Patient specific instrumentation (hereinafter "PSI") pertains to the creation of instruments that are made specifically for the patient. PSI are typically manufactured from data using imagery to model bone geometry. Therefore, PSI have surfaces that may contact the bone in a predictable way as such contact surfaces are specifically manufactured to match the surface of a bone. It would therefore be desirable to use PSI technology in shoulder surgery.

SUMMARY OF THE APPLICATION

It is therefore an aim of the present disclosure to provide a method for performing glenoid implant surgery using patient specific instrumentation.

It is a further aim of the present disclosure to provide patient specific instrumentation for glenoid implant surgery.

Therefore, in accordance with one aspect of the present invention, there is provided a pin placement instrument for placing a pin in a bone comprising: an anatomical interface with a hook-like portion being opened in a lateral direction of the instrument to receive a bone therein in a planned position; a drill guide connected to the anatomical interface and defining at least one guide slot in a longitudinal direction of the instrument, the at least one guide slot having a lateral opening over its full length in the drill guide to allow lateral withdrawal of the instrument in said lateral direction with the pin placed in the bone passing through the lateral opening; and at least one bushing removably placed in said guide slot via said longitudinal direction in a planned fit, the bushing defining a throughbore aligned with the guide slot and adapted to receive the pin extending in said longitudinal direction when the bushing is in the guide slot for pin placement.

Further in accordance with aspect of the present disclosure, wherein the drill guide comprises two of said guide slot.

Still further in accordance with aspect of the present disclosure, the two said guide slots are parallel to one another.

Still further in accordance with aspect of the present disclosure, the at least one bushing has an abutment end for limiting movement in the longitudinal direction when placed in the guide slot.

Still further in accordance with aspect of the present disclosure, a socket in the drill guide is adapted to receive a handle for distal manipulation.

Still further in accordance with aspect of the present disclosure, at least one said pin is provided for each set of the guide slot and the bushing, the bushing being in sliding engagement on the pin.

Still further in accordance with aspect of the present disclosure, surfaces of the hook-like portion are generally transverse to the longitudinal direction.

Still further in accordance with aspect of the present disclosure, the hook-like portion has at least one patient specific surface based on an anatomical model of the patient.

Still further in accordance with aspect of the present disclosure, the anatomical model of the patient is that of a scapula, the at least one patient-specific surface being complementary to a shape of at least one of the scapula head and glenoid neck.

Still further in accordance with aspect of the present disclosure, the at least one guide slot is longitudinally aligned with at least one of a planned center of an implant, a location adjacent to the superior glenoid rim in alignment with the coracoid, and a base of the coracoid.

Therefore, in accordance with another aspect of the present disclosure, there is also provided a method for resurfacing a glenoid, comprising: obtaining a patient specific instrument with at least two pin slots; installing a pin slot of the patient specific instrument over a first pin secured to the scapula; installing a cannulated reamer over a second pin secured to the glenoid; installing a shaft slot of the patient specific instrument over a shaft of the cannulated reamer to form a joint between the shaft slot and the shaft of the cannulated reamer allowing a translational movement of the cannulated reamer along the second pin; and reaming the glenoid using the cannulated reamer as guided by the patient specific instrument and the pins.

Further in accordance with this other aspect of the present disclosure, obtaining the patient specific instrument comprises obtaining the patient specific instrument with an end of the shaft slot distal from the glenoid at a patient specific distance from the glenoid, and further comprising stopping a reaming once a stopper on the shaft of the cannulated reamer abuts the end of the shaft slot.

Still further in accordance with aspect of the present disclosure, the method comprises obtaining the cannulated reamer with the stopper on the shaft at a patient specific distance as a function of a planned depth of reaming.

Still further in accordance with aspect of the present disclosure, installing the shaft slot of the patient specific instrument over the shaft of the cannulated reamer comprises rotating the patient specific instrument about the first pin for the shaft of the cannulated reamer to be received in the shaft slot via a lateral opening in the shaft slot.

In accordance with yet another aspect of the present disclosure, there is provided a method for positioning an implant in a resurfaced glenoid cavity, comprising: obtaining a patient specific instrument with at least one pin slot; installing the pin slot of the patient specific instrument over a pin secured to the scapula; installing a shaft of an impactor in a guide bracket of the patient specific instrument such that the shaft is aligned with the resurfaced glenoid cavity, a translational joint being formed between the shaft and the guide bracket allowing a translational movement of the shaft along the guide bracket; installing the implant at the free end of the impactor; and forcing the implant into the resurfaced glenoid cavity as guided by the patient specific instrument and the pin.

Still further in accordance with aspect of the present disclosure, obtaining a patient specific instrument comprises obtaining a patient specific orientation of the guide bracket such that an orientation of throughbores in the implant relative to the resurfaced glenoid cavity is as a function of planned positioning of screws received in the throughbores of the implant.

Still further in accordance with aspect of the present disclosure, the method further comprises positioning a drill guide in the implant forced into the resurfaced glenoid cavity, the drill guide comprising a visual pointer positioned to point toward the pin.

Still further in accordance with aspect of the present disclosure, forcing the implant into the resurfaced glenoid cavity as guided by the patient specific instrument and the pin comprises moving the implant in a single translation degree of freedom.

DESCRIPTION OF THE EXEMPLARY EMBODIMENTS

Figure 1:
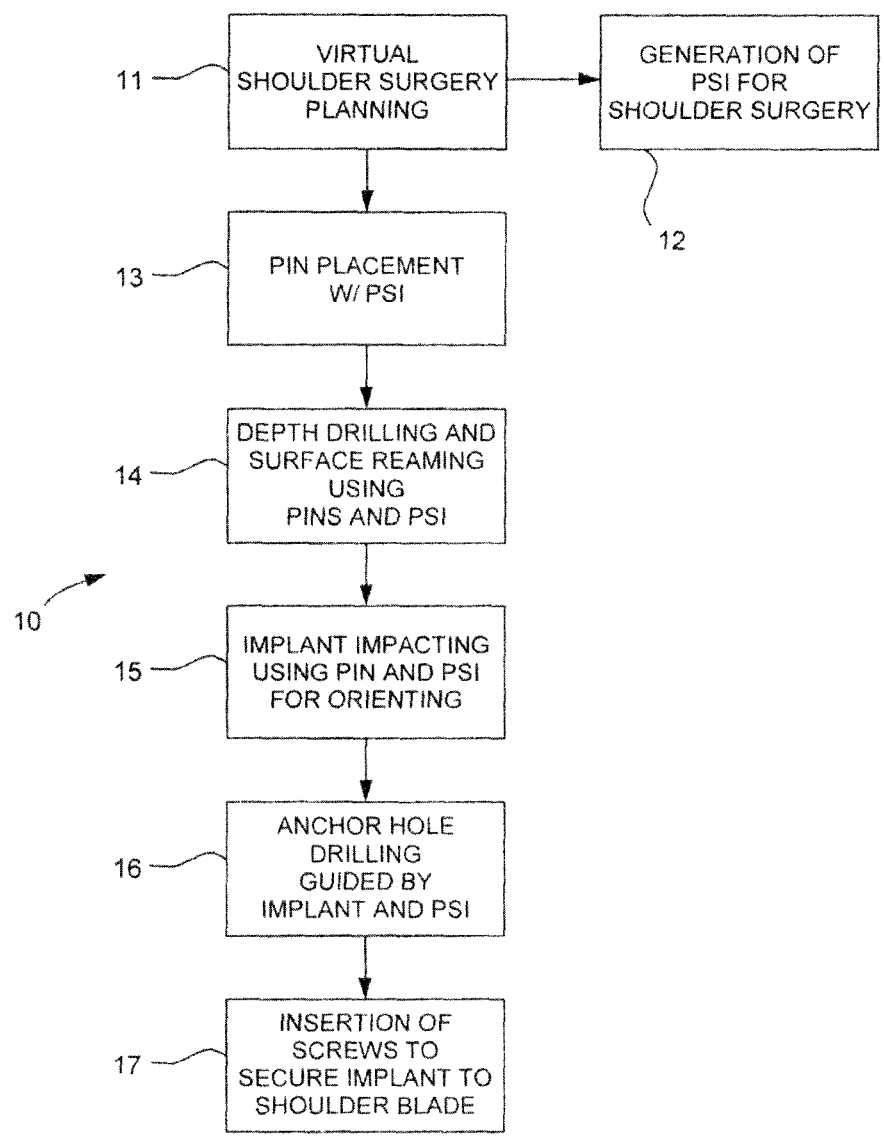
FIG. 1 is a flowchart of a method for securing a glenoid implant on a scapula, using patient specific instrumentation.

Referring to the drawings and more particularly to FIG. 1, there is illustrated at 10 a method for securing a glenoid implant on a scapula (i.e., scapula) In order to perform the method, patient specific instrumentation of various kinds are used, and will be referred to hereinafter as PSI, with reference to FIGS. 2-13. By way of example, FIG. 2 features the positioning of a glenoid hemispherical head implant base on the scapula, in reverse total shoulder surgery. However, the method 10 may alternatively be used to secure a cup implant in the glenoid as performed on anatomic total shoulder replacement.

According to step 11 of FIG. 1, virtual shoulder surgery planning is performed. In this planning step, various shoulder structures are displayed as three-dimensional models, along with a model implant and its components. These 3-D models are typically the result of the processing pre-operative imagery (e.g., CT scans, MRI, etc) and hence are a precise and accurate representation of a patient's bones.

During the planning step, the operator may select various types and dimensions of implants and interactively plan where the implant and its components will be located on the scapula and humerus. In the case of the glenoid implant, the position and orientation thereof may include a virtual representation of the position and orientation of the screws that will secure the glenoid implant to the scapula. Due to the length of the screws and the thinness of the scapula medial to the glenoid, the virtual planning of the location of the glenoid implant typically aims at finding an orientation and depth for the screws that will not have them pierce through the bone material.

Figure 2:
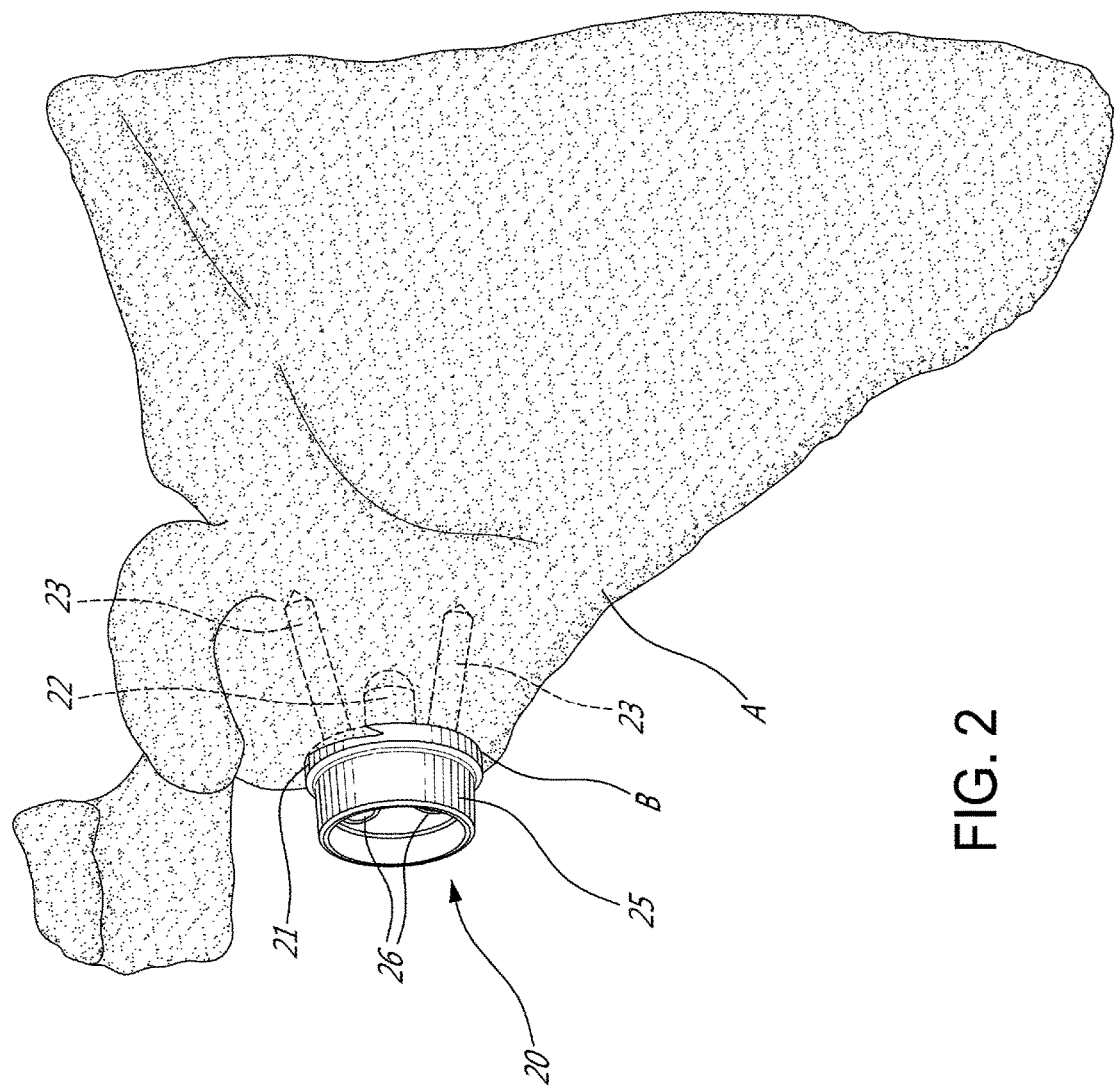
FIG. 2 is a perspective view of a scapula with a glenoid implant, in virtual planning.
Figure 9:
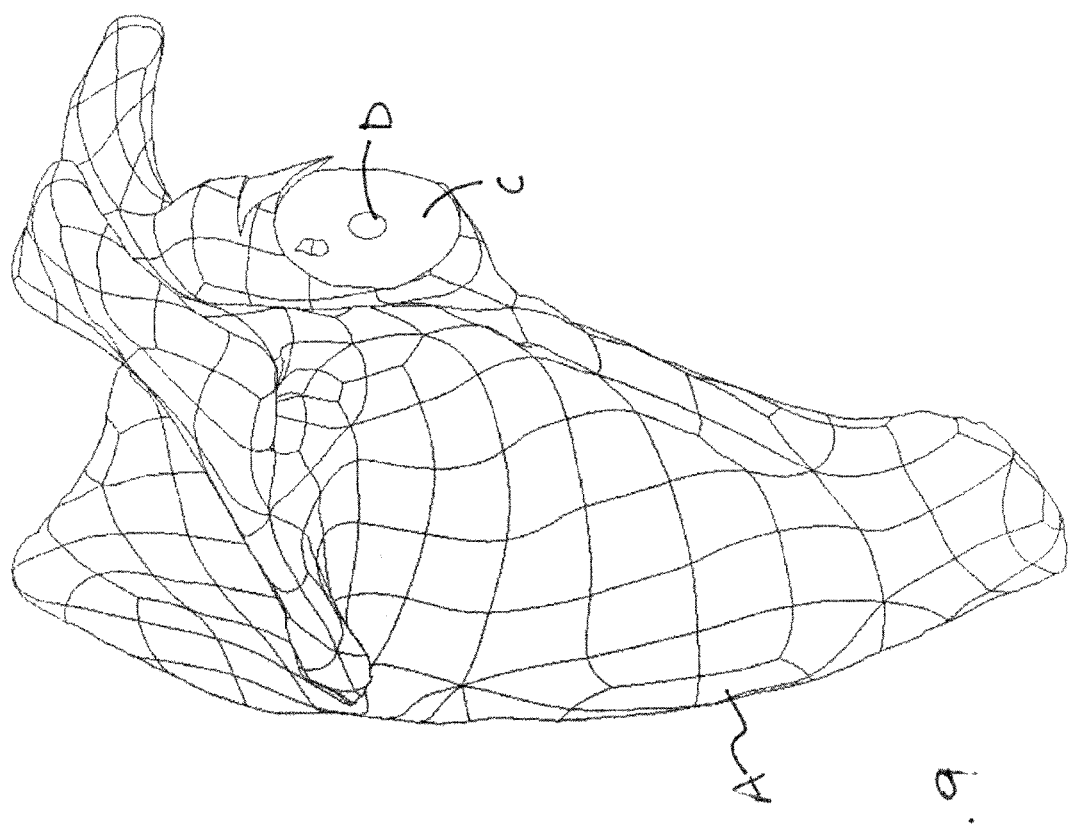
FIG. 9 is a perspective view of the scapula with the reamed glenoid.
Figure 14:
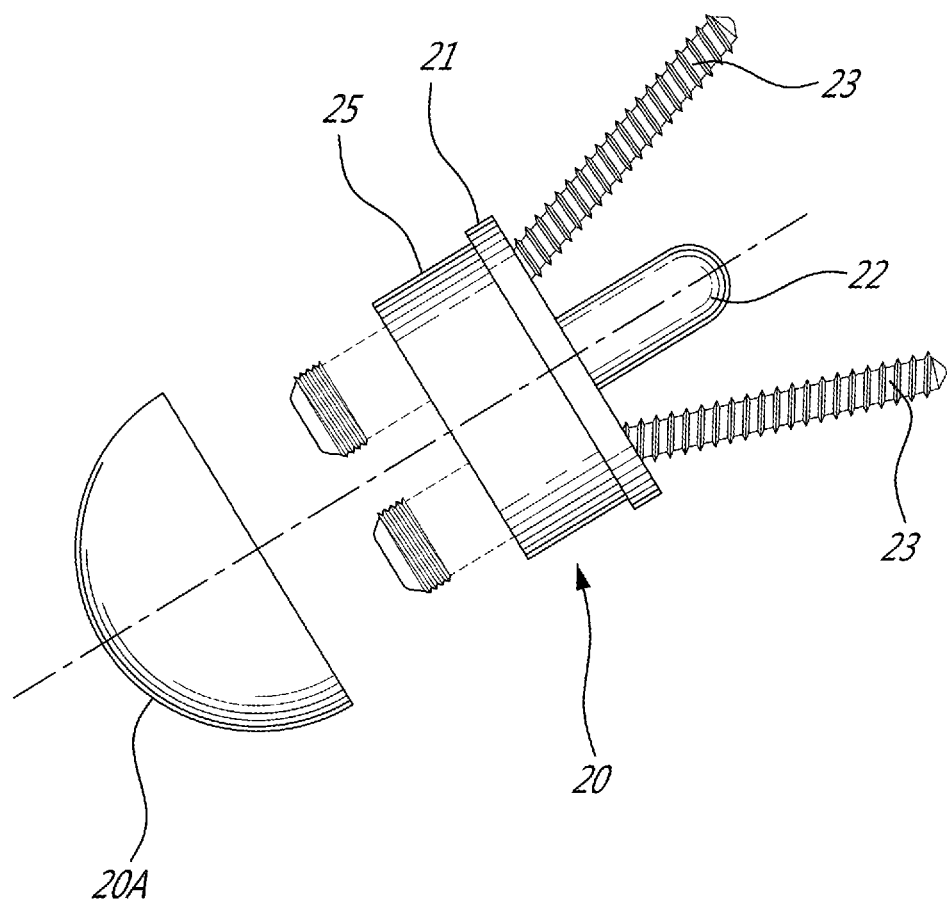
FIG. 14 is an assembly view of a glenoid hemispherical implant.

For example, there is illustrated at FIG. 2 a model of the scapula A of the patient with parts of an implant 20 (also shown in FIG. 14), the implant 20 being of the ball head type (i.e., a hemispherical head 20A). The implant 20 comprises a base plate 21. The base plate 21 is of the type made of a metal that will be adhered and fitted in a resurfaced glenoid cavity C (FIG. 9). For instance, a trabecular-like medical grade metal may be used for the base plate 21. A peg 22 projects from an underside of the base plate 21 and will be accommodated in a bore drilled in the glenoid cavity B. Screws 23 also project from the underside of the base plate 21 and anchor the implant 20 to the scapula A. A body 25 is secured to the base plate 21, as these parts are generally monolithic The body 25 is the interface of the implant 20 with a hemispherical ball head that will define the surface contacting the humerus or implant thereon. Throughbores 26 are hence concurrently defined in the body 25 and base plate 21, with the screws 23 passing through these throughbores 26.

Steps 12 to 17 of the method 10 are used to guide the surgeon or operator in performing bone alterations so as to replicate the virtual shoulder surgery planning of step 11. Hence, steps 12 to 17 the method 10 are performed to ensure that the glenoid implant is installed substantially similarly to the virtual planning.

Figure 15:
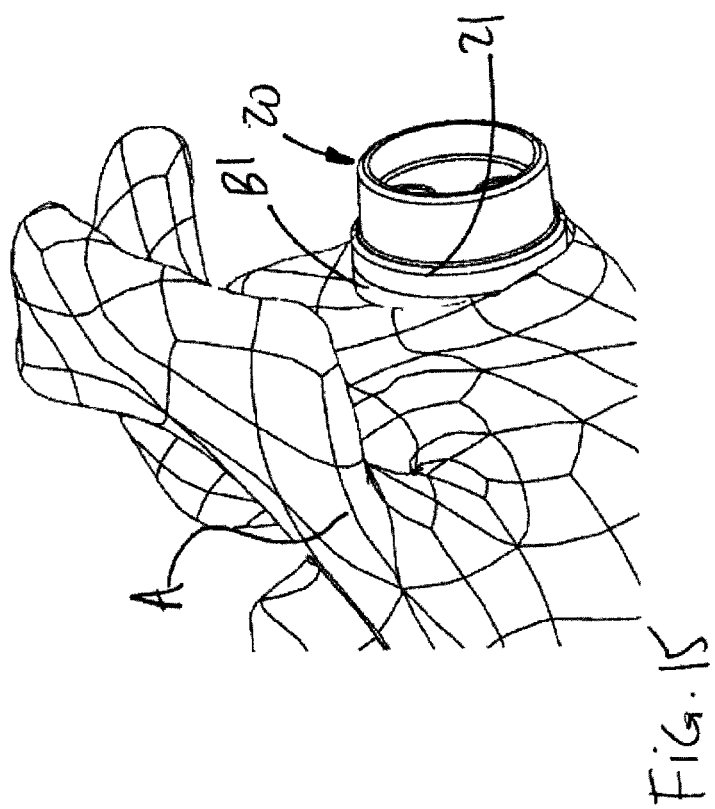
FIG. 15 is a perspective view of a scapula with a glenoid implant and a graft.

According to step 12, PSI are generated using the data obtained from the virtual planning. The PSI will be described in further detail hereinafter. Any appropriate manufacturing method and materials may be used for the PSI, provided that the PSI are precise and accurate representations of the PSI required as a result of the virtual planning. The generation of PSI according to step 12 is performed preoperatively using the imagery data that is also used for the step 11 of virtual shoulder surgery planning. Any other source of anatomical data may also be used, such as manual bone measurements, obtained preoperatively. Another information that may be obtained via the planning step is the generation of a required graft. It may be required to use a graft wedge B1 between the implant and the scapula, and the planning step may therefore define a model of required graft, as shown in FIG. 15, as well as a PSI tool to shape the graft wedge B1 to a predetermined geometry calculated in the virtual planning. The graft wedge B1 would be positioned between the implant 20 and the machined glenoid cavity C. The use of a graft may be required for scapulas limited to a shallow glenoid cavity C, i.e., that does not have a full counterbore shape. Hence, as shown in FIG. 15, the graft wedge B1 would form concurrently with the cavity C the surface against which the implant 20 is applied.

Steps 13 to 17 are performed intra-operatively. The steps are performed once the shoulder joint has been exposed and the humerus has been dislocated, resected and/or separated from the scapula A (FIG. 2).

Figure 3:
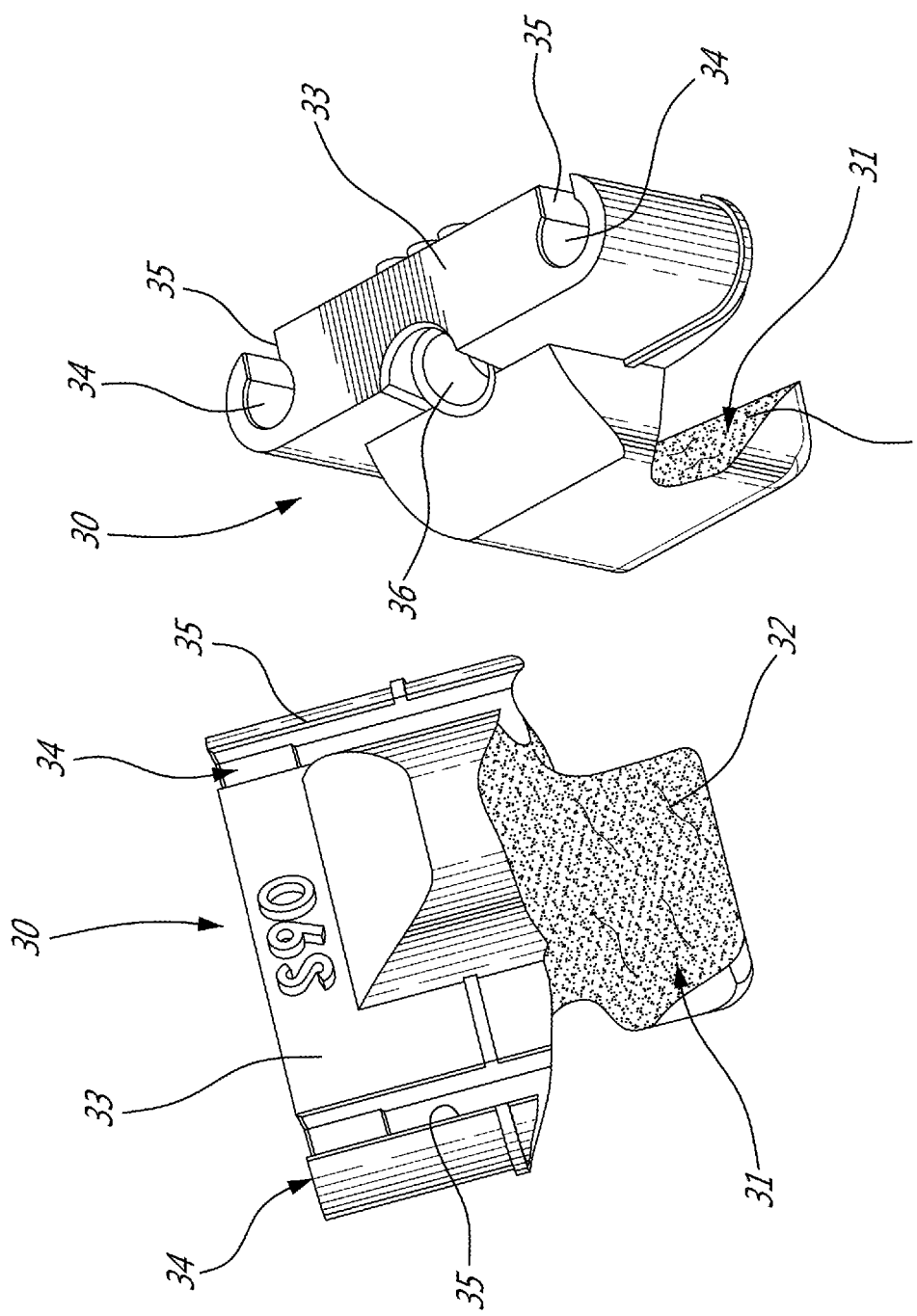
FIG. 3 is a pair of perspective views of a pin placement PSI in accordance with an embodiment of the present disclosure.
Figure 4:
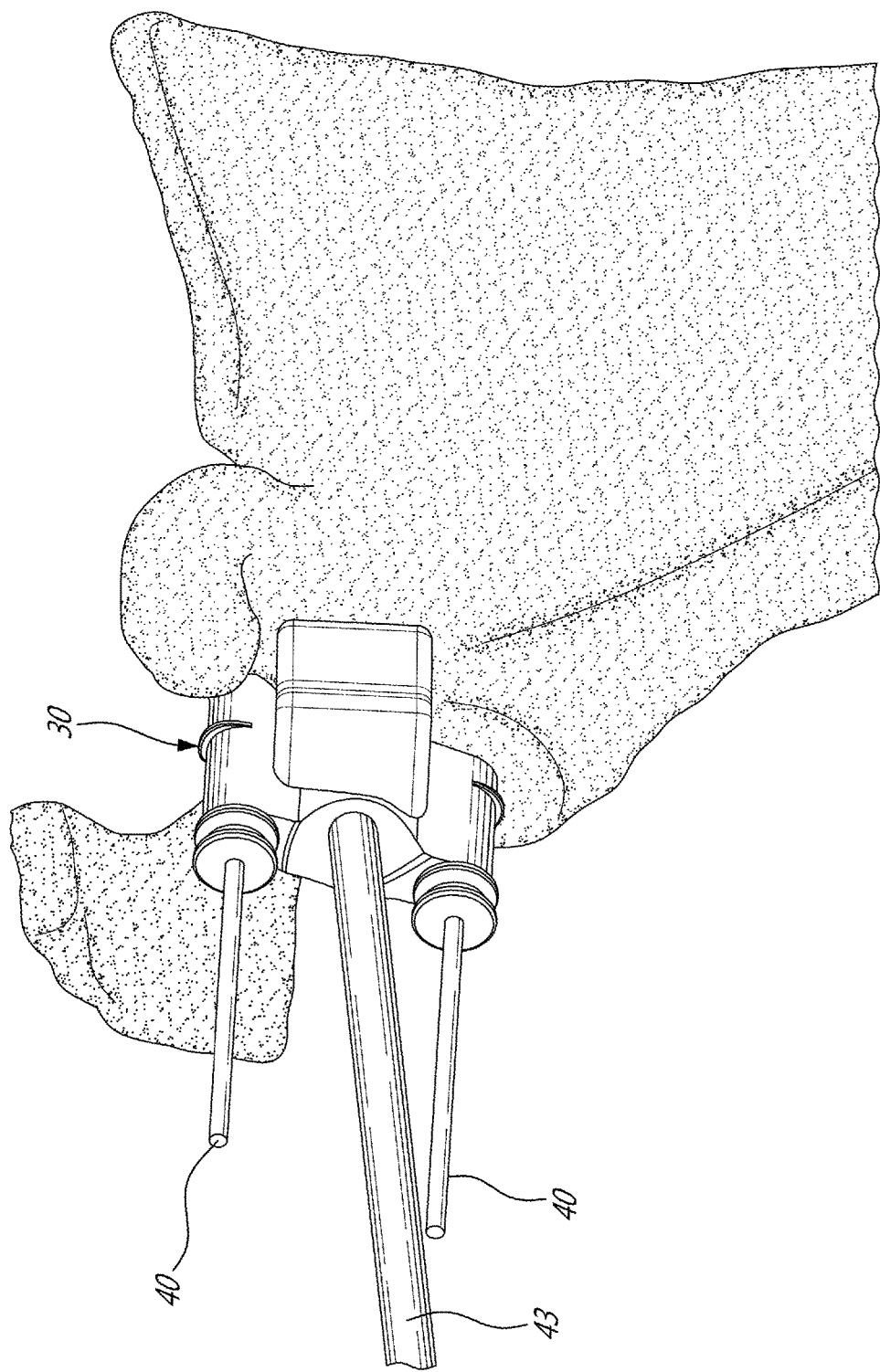
FIG. 4 is a perspective view of the scapula with the pin placement PSI of FIG. 3, during placement of pins.

According to step 13 (FIG. 1), a pair of pins are placed in the scapula A using PSI. Referring concurrently to FIGS. 3 and 4, a pin placement PSI is generally shown at 30. The pin placement PSI 30 comprises an anatomical interface 31. The anatomical interface 31 has a laterally opened hook-like shape so as to receive therein both sides of the scapula head and/or neck of the glenoid B. In accordance with PSI, the anatomical interface 31 has a contact surface(s) 32 that is manufactured to match the corresponding surface on the patient's scapula. Accordingly, the positioning of the pin placement PSI 30 will be guided by the contact surface 32 finding its corresponding matching surface on the scapula A.

The pin placement PSI 30 further comprises a drill guide 33. The drill guide 33 is positioned relative to the anatomical interface 31 as a function of the virtual planning of step 11 (FIG. 1). The drill guide 33 has a pair of cylindrical cutouts or slots 34 that are specifically positioned and oriented to guide the drilling of the pins in the glenoid B, i.e., the slots 34 extend in the longitudinal direction of the PSI 30. According to an embodiment, lateral openings 35 allow lateral access to the slots 34 such that the pins may be laterally inserted into the slots 34. A socket 36 or like connector may also defined in the drill guide 33 to facilitate the manipulation of the pin placement PSI 30. For instance, an elongated tool may be connected to the pin placement PSI 30 by way of the socket 36, for its distal manipulation.

Figure 5:
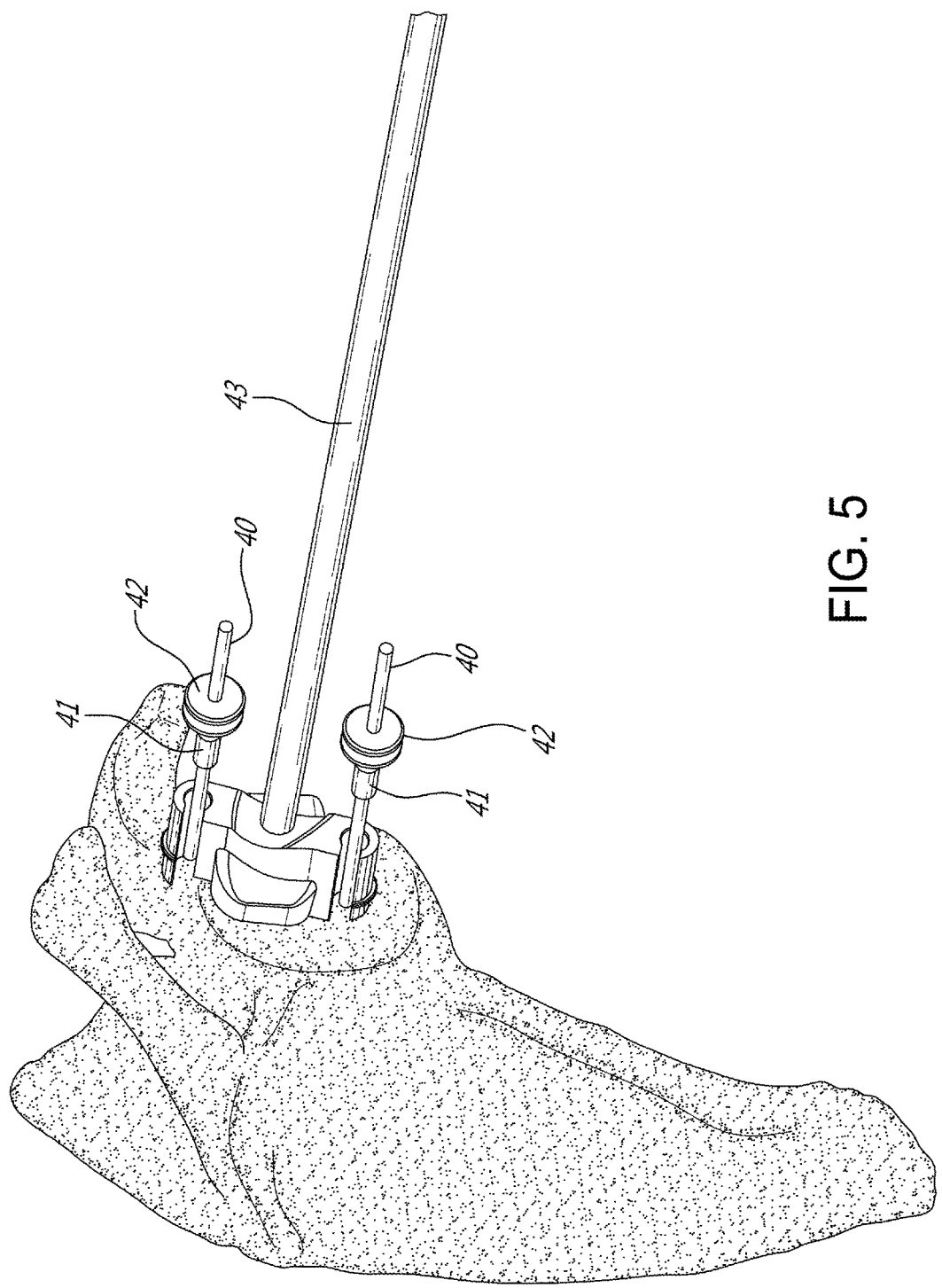
FIG. 5 is a perspective view of the scapula of FIG. 4, during the removal of the pin placement PSI.

As shown concurrently in FIGS. 4 and 5, pins 40 are drilled into the scapula A. The pins 40 may be provided with sleeves 41 (a.k.a., bushings) received in a planned fit (e.g., precise fit) that will ensure that the pins 40 are axially centered in the slots 34, as the sleeves 41 have throughbores centered with the slots 34. Moreover, the sleeves 41 may comprise abutment ends 42 to control the depth of insertion of the pins 40 in the glenoid. Any appropriate methods are also considered to control the depth of insertion of the pins 40, such as graduating the pins 40 with a scale, etc.

In operation, handle 43 is connected to the socket (FIGS. 3 and 4), and the pin placement PSI 30 is installed onto the glenoid B with the anatomical interface ensuring that the pin placement PSI 30 is properly positioned on the scapula A, by laterally moving the pin placement PSI 30 into planned position on the bone. The pins 40 with sleeves 41 thereon are inserted in the slots 34 of the pin placement PSI via the lateral openings 35, and may hence be drilled into the glenoid B, or the sleeves/bushings 41 may be placed in the slots 34 prior to threading the pins 40 therein. Once the pins 40 are suitably inserted in the scapula A, the sleeves 41 may be withdrawn by sliding them off the end of the pins 40 shown in FIG. 5, thereby allowing the removal of the pin placement PSI 30 from the scapula A by a lateral movement. The surfaces of the hook-like portion of the anatomical interface 31 are generally transverse to a longitudinal direction of the drill guide 33. The presence of the lateral openings 35 allows a good contact surface between the hook-like portion of the anatomical interface 31, without having difficulties in the lateral withdrawal of the PSI 30 as the pins 40 pass through the lateral openings 35.

Figure 16:
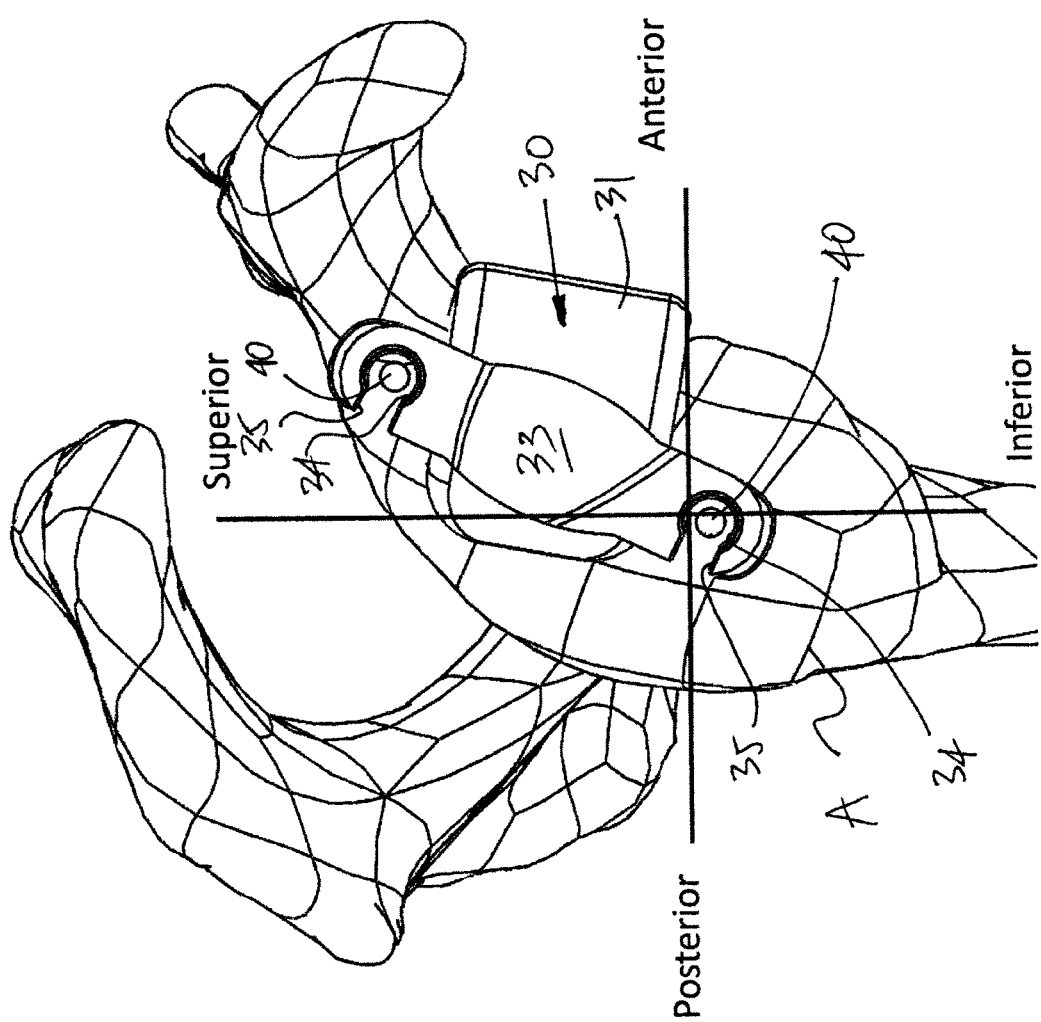
FIG. 16 is a lateral view of a pin placement PSI of FIG. 4, on the scapula.

According to the illustrated embodiment, one of the pins 40 is at a center of the anticipated resurfaced glenoid cavity C, while the other pin 40 is located adjacent to the superior glenoid rim in alignment with the coracoid or at the base of the coracoid. Other positions are also considered. For illustrative purposes, a contemplated position of the pin placement PSI 30 is generally shown relative to the scapula A in FIG. 16.

Figure 6:
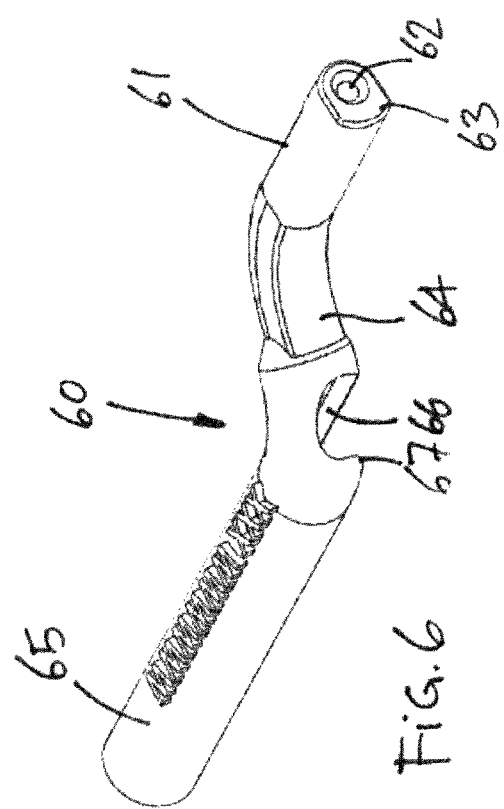
FIG. 6 is a perspective view of a depth drilling PSI in accordance with another embodiment of the present disclosure.
Figure 7:
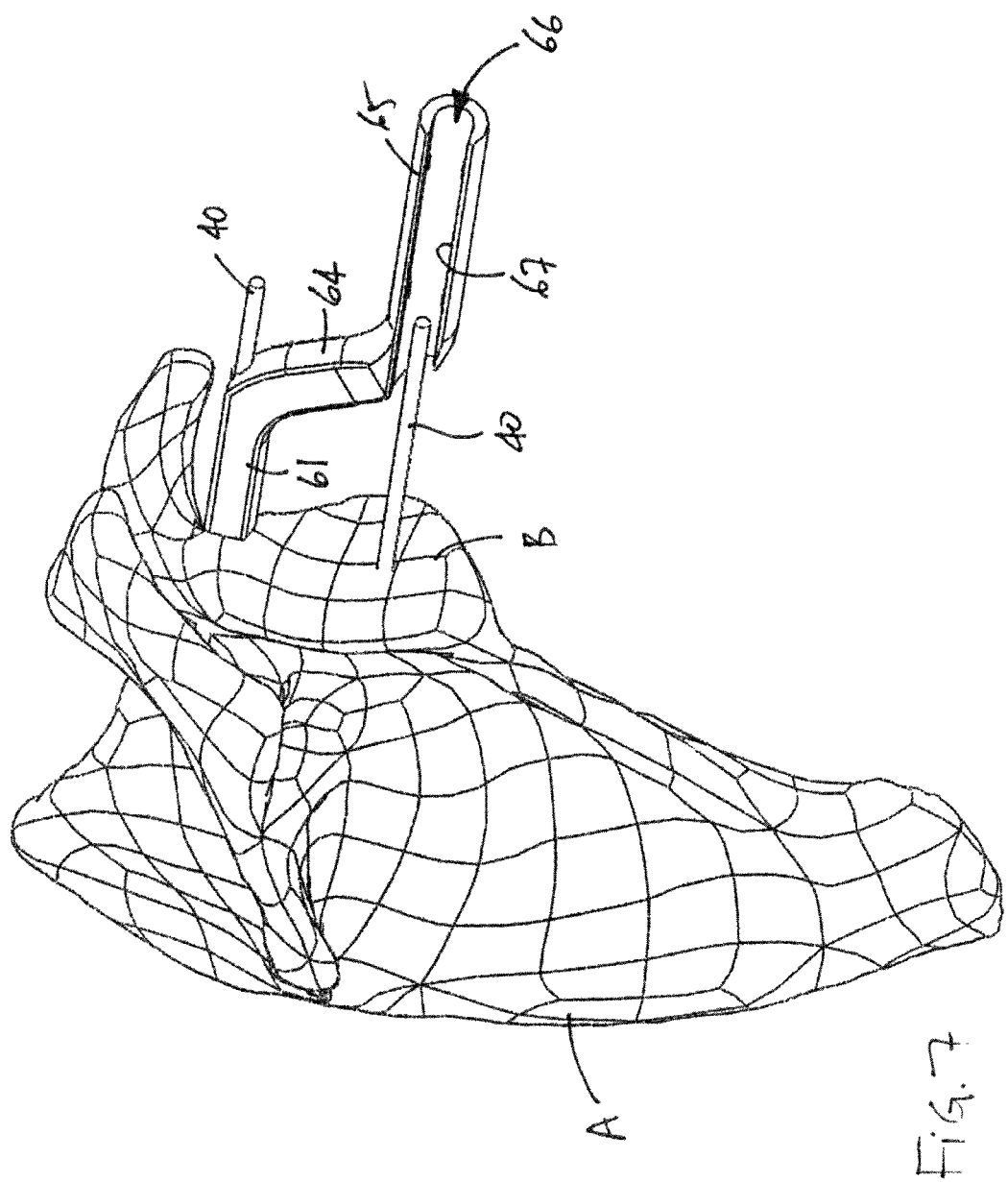
FIG. 7 is a perspective view of the scapula with the depth drilling PSI of FIG. 6.

Referring to FIG. 1, a step 14 of depth drilling and/or surface reaming on the glenoid B is performed using the pins 40 and an appropriate PSI. Referring concurrently to FIGS. 6 and 7, a reaming PSI is generally shown at 60. The reaming PSI 60 has a first tube 61 with a pin slot 62 that is dimensioned to be slid onto one of the pins 40, thereby forming a cylindrical joint therewith. An end of the first tube 61 defines an abutment 63 to abut against the scapula A. A spacing arm 64 extends laterally from the first tube 61 and has at its free end a second tube 65. The second tube 65 also comprises a shaft slot 66, which shaft slot 66 is laterally accessible via a lateral opening 67, used to rotate the reaming PSI 60 such that the pin 40 enters the shaft slot 66. As the reaming PSI 60 is patient specific, the pin slots 62 and the shaft slot 66 are spaced apart by a predetermined distance to match the spacing between the pins 40. Hence, as shown in FIG. 7, when the first tube 61 is slid onto one of the pins 40, the other pin 40 may be oriented to be within the shaft slot 66 of the second tube 65.

It is pointed out that step 14 may comprise a verification of the location of the pins 40. As the reaming PSI 60 is fabricated to receive the pins 40, the centrally-located pin 40 should be axially centered in the second tube 65. Any off-centering may indicate improper positioning of the pin 40, and such indication may cause a review of step 13 to reposition the pins 40.

Figure 8:
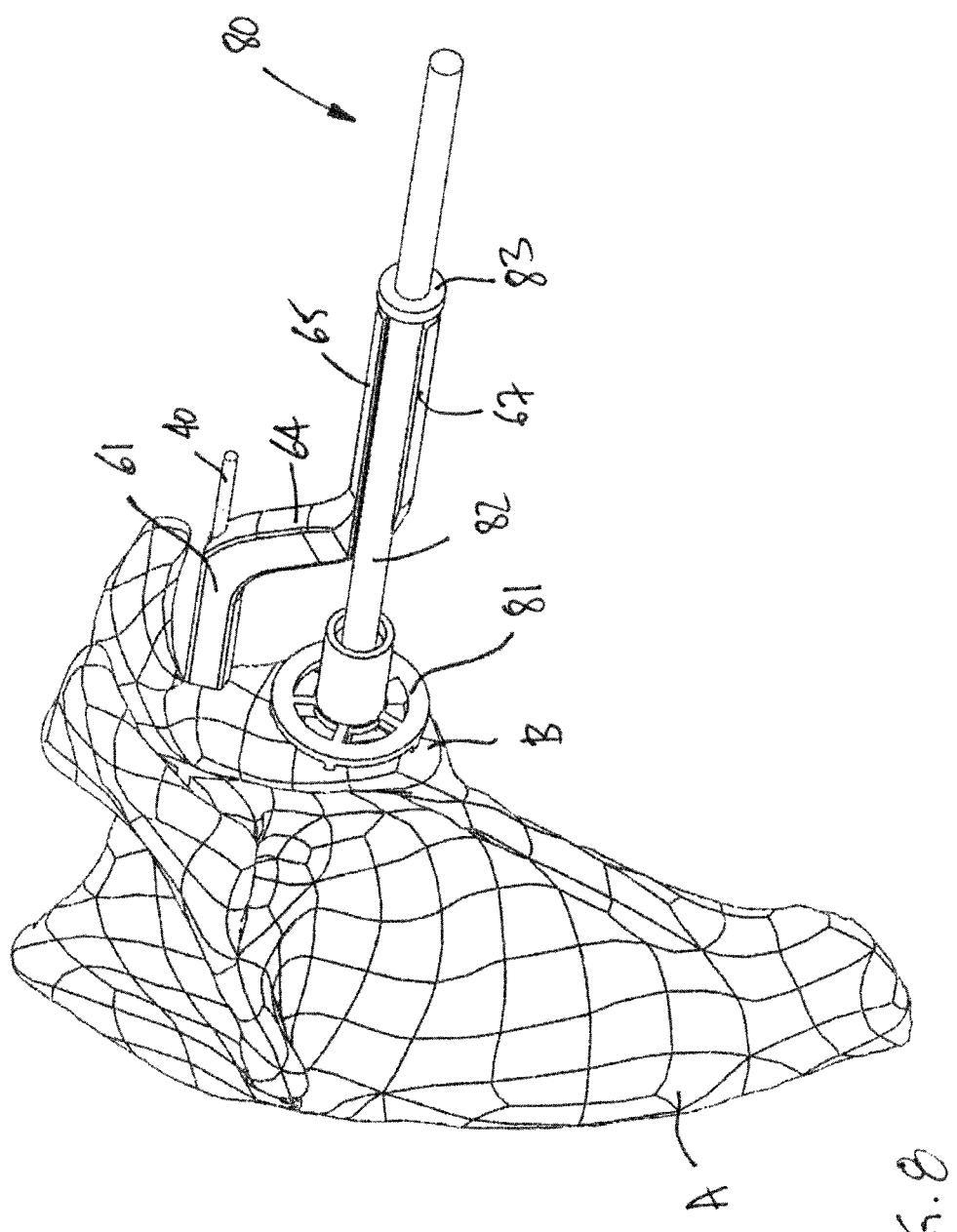
FIG. 8 is a perspective view of the scapula and depth drilling PSI, with a cannulated reamer.

Referring to FIG. 8, a cannulated reamer 80 may therefore be installed onto the pin 40 that is within the shaft slot 66, so as to be coaxially guided by the pin 40 in translation. The reamer 80 has a reamer end 81 that is selected to perform resurfacing of a planned diameter in the glenoid B. The reamer end 81 is located at the end of a shaft 82. The shaft 82 is sized to be received in the shaft slot 66 of the reaming PSI 60, to form the translational joint. Moreover, the reamer end 81 may also drill a bore of sufficient diameter to receive the peg 22 of the implant 20 therein (FIG. 2), to a depth defined by abutment against the reaming PSI 60. The drilling of the peg bore may alternatively be done separately. Accordingly, the combination of the pin 40 in the cannulated reamer 80 and the cooperation between the shaft 82 and the shaft slot 66 ensures that the glenoid B is reamed specifically where desired to a desired depth. The shaft 82 enters the shaft slot 66 by being slid or snapped into it. Still referring to FIG. 8, a stopper 83 may be installed on the end of the shaft 82. The stopper 83 cooperates with the reaming PSI 60 to limit the depth of penetration of the reamer 80 in the glenoid B, to ensure that the surface reaming and optional depth drilling (if done separately for the peg 22 of FIG. 2) have a planned depth.

It is observed that both pins 40 are used to support the reaming PSI 60 and guide movement of the cannulated reamer 80. By using both pins 40, the structural integrity of the pin 40/PSI 60 assembly is increased over a single pin 40. However, it is considered to use any other configuration, for instance using a single pin 40, with the cannulated reamer 80, the reamed the glenoid B.

As shown in FIG. 9, once the glenoid B has been reamed to define the resurfaced glenoid cavity C with peg bore D, the depth drilling PSI 60 may be removed along with the pins 40. Although not shown, it may be desired to keep the pin 40 that is not in the resurfaced glenoid cavity C, as explained hereinafter. In the case in which the wedge graft B1 is used (FIG. 15), the wedge graft B1 is installed at the adequate position on the glenoid B, adjacent to the resurfaced glenoid cavity C. The pin 40 on the coracoid may be used to guide an operator in properly orienting the wedge graft B1. The wedge graft B1 may be fused to the glenoid B, and the screws 23 will secured both the implant 20 and the wedge graft B1 to the glenoid B.

Referring to FIG. 1, a step 15 of impacting the implant 20 is performed, using one of the pins and PSI for properly orienting the implant 20. More specifically, the orientation of the implant 20 will have an impact on the positioning of the screws 23 (FIG. 2). Hence, in order to replicate the virtual planning of step 11, the implant 20 must be correctly oriented so as to have the throughbores 26 aligned with the planned location of insertion of the screws 23.

Figure 10:
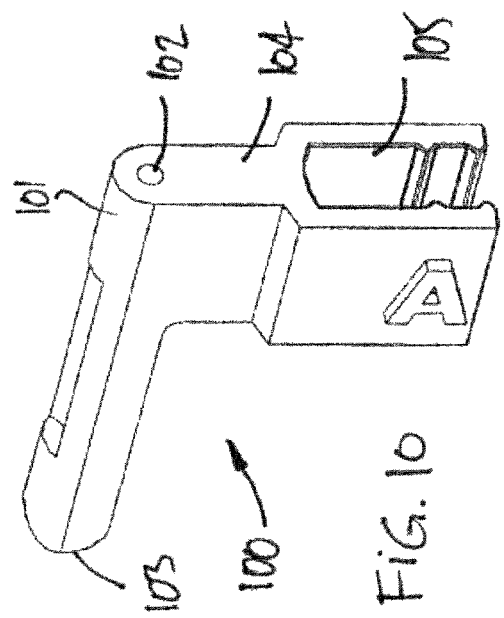
FIG. 10 is a perspective view of an impactor guide PSI in accordance with yet another embodiment of the present disclosure.
Figure 11:
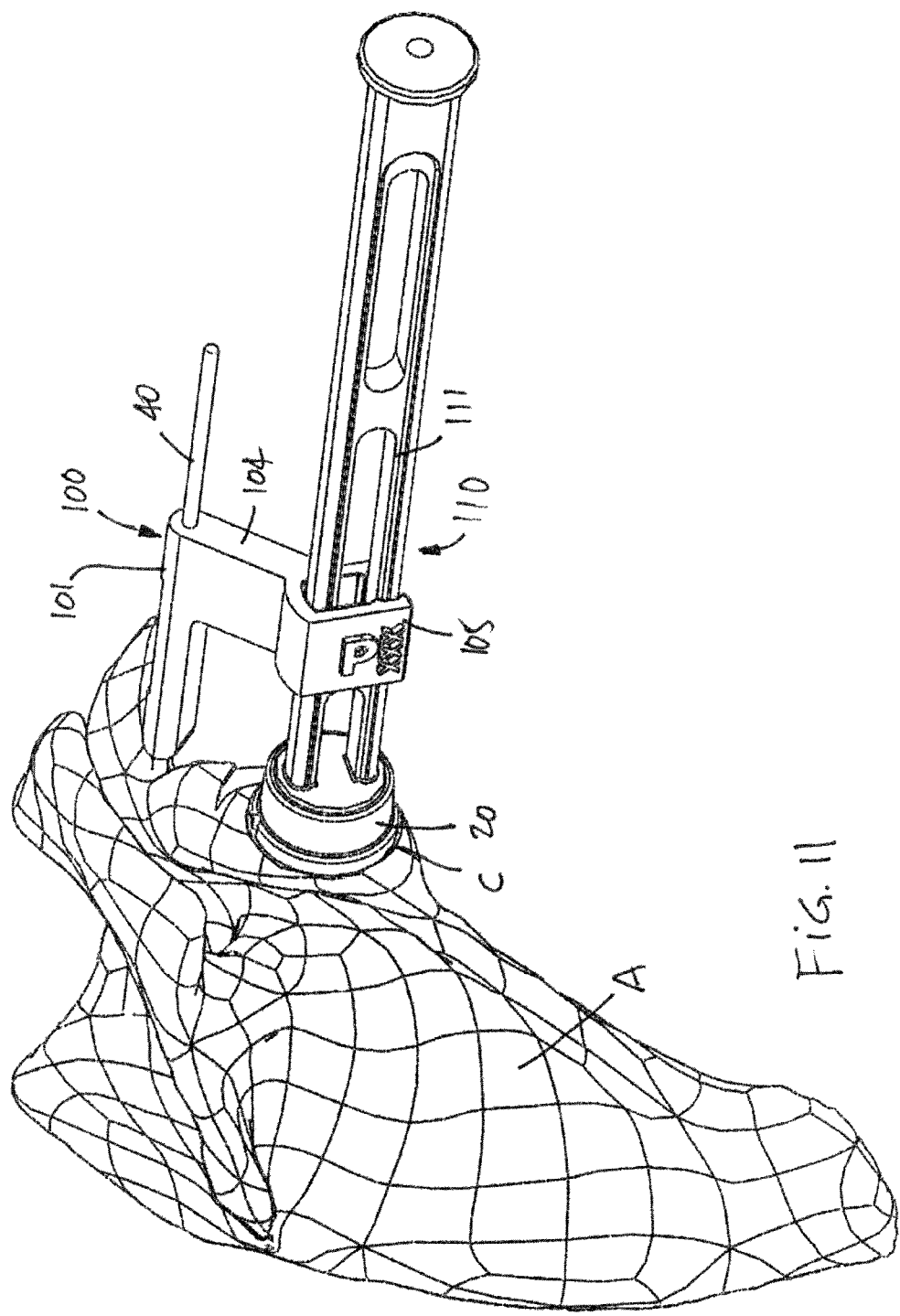
FIG. 11 is a perspective view of the scapula with the impactor guide PSI and impactor tool.

Referring concurrently to FIGS. 10 and 11, an impacting guide PSI is generally shown at 100. The impacting guide PSI 100 comprises a tube 101 with a pin slot 102. The pin slot 102 is sized so as to receive therein the remaining pin 40 and form therewith a cylindrical joint. An abutment end (with any appropriate shape/geometry) 103 of the tube may have a patient-specific contact surface shaped to rest against a surrounding bone surface and hence prevent rotation of the PSI 100 when the tube 101 abuts the bone. An arm 104 projects laterally from the tube 101. A guide bracket 105 is at a free end of the arm 104 and is used to guide the movement of an impactor tool 110. More specifically, the guide bracket 105 has a lateral opening for receiving therein a shaft 111 of the impactor tool 110 to form a sliding joint therewith.

The impactor tool 110 may be conventional, with a pair of pegs spaced apart to be received in the throughbores 26 of the implant 20 (FIG. 2). The guide bracket 105 is specifically oriented as a function of a location of these pegs at the end of the shaft 111 of the impactor tool 110, to control the positioning of the throughbores 26 of the implant 20, in accordance with the virtual planning step 11 (FIG. 1).

Hence, with the assembly of FIG. 11, the implant 20 may be inserted into the resurfaced glenoid cavity C. The matching shape of the implant 20 and resurfaced glenoid cavity C may result in a self-centering of the implant 20 during impacting (and therefore not necessitating the patient-specific surface at the abutment end 103 to perform an alignment). However, the PSI 100 and impactor tool 110 generally ensure that the implant 20 is fully inserted in the resurfaced glenoid cavity C, with the throughbores 26 located where planned. At this point, the PSI 100 may be removed with the impactor tool 110 leaving the implant 20 in the resurfaced glenoid cavity C.

Figure 12:
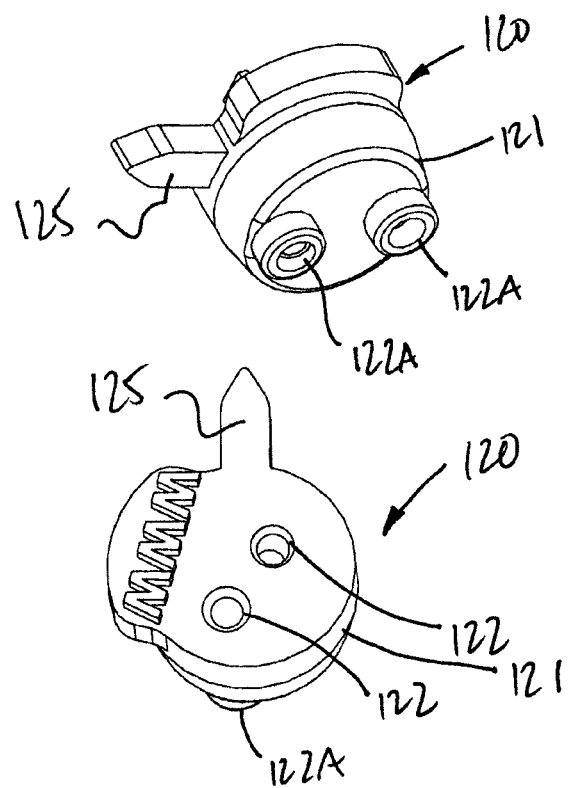
FIG. 12 is a perspective view of a drilling guide PSI in accordance with yet another embodiment of the present disclosure.
Figure 13:
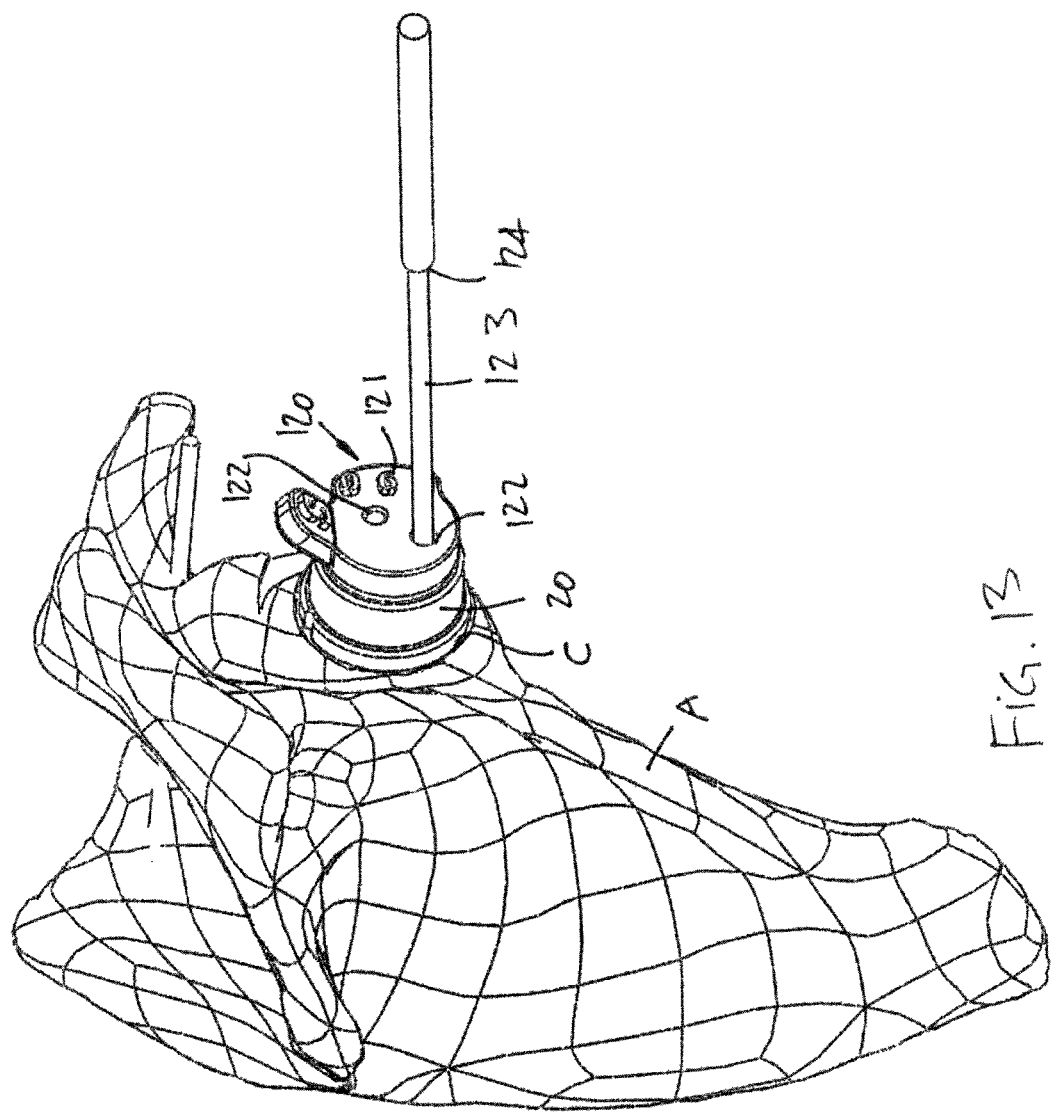
FIG. 13 is a perspective view of the scapula with the drilling guide PSI and drill bit.

According to step 16 of FIG. 1, anchor holes may be drilled in the glenoid as planned, for the subsequent insertion of the screws 23. Referring to FIGS. 12 and 13, a drill guide PSI 120 has a body 121 sized to be received in a corresponding cavity in the implant body 25. A pair of drill guide bores 122 are defined in the body 121 of the drill guide PSI 120. The drill guides bores 122 are specifically located and oriented to have guiding cylinders 122A in axial extension of the throughbores 26 in the implant 20 (FIG. 2). Moreover, the diameter of the guiding cylinders 122A is generally tapering to center a drill bit 123 therein, to reduce any potential play between the drill bit 123 and the drill guide bores 122. The material used for the body 121 of the drill guide PSI 120 may also be selected so as not to be damaged by the drill bit 123. As shown in FIG. 13, a stopper 124 may be provided on the drill bit 123 to control the drilling depth to reach the planned depth for the anchor holes. Alternative methods are considered as well, such as graduating the drill bit 123 with a scale, to control the depth. Once the anchor holes have been drilled, the drill guide PSI 120 may be removed. As shown in FIG. 12, the drill guide PSI 120 may also comprise a visual pointer 125. The visual pointer 125 may be patient-specifically formed in the drill guide PSI 120 to point at the remaining pin. This therefore represents an additional verification step to ensure that the holes are drilled at the desired location.

According to step 17 of FIG. 1, screws 23 (or like fasteners) may secure the implant 20 to the scapula A, replicating the virtual planning of FIG. 2. Conventional steps are then performed to finalize the shoulder surgery.

It is pointed out that the method 10 may include a step of creating the graft B1 of FIG. 15. The step of method 10 may include providing a PSI tool for the removal of bone material, for instance from the humerus, as the humerus must be resurfaced. However, the graft B1 removed from the humerus or other bone may simply have a cylindrical shape, and hence a standard cylindrical reamer of appropriate diameter may be used. As the graft B1 is shown as having a wedge shape in FIG. 15, an appropriate PSI tool may be created to machine the oblique plane of the graft B1.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A pin placement instrument for placing at least one pin in a scapula comprising:
    an anatomical interface with a hook-like portion being opened laterally relative to the instrument to receive a bone therein in a predetermined position, the hook-like portion having a first surface modeled specifically to match an upper surface of the scapula of a patient, and a second surface modeled specifically to match an under surface of the scapula opposite the upper surface in a longitudinal direction of drilling whereby the hook-like portion is configured to hook onto both sides of a portion of the scapula;
    a drill guide connected to the anatomical interface and defining at least one guide slot in the instrument and configured to be positioned on the upper surface of the scapula, the at least one guide slot having a lateral opening over its full length in the drill guide to allow lateral withdrawal of the instrument in a lateral direction from hooking engagement with the scapula when the at least one pin is placed in the scapula and is passing through the lateral opening; and at least one bushing removably placed in said at least one guide slot, the at least one bushing defining a throughbore aligned with the at least one guide slot and adapted to receive the at least one pin extending longitudinally in the instrument when the at least one bushing is in the at least one guide slot for pin placement, the at least one bushing having an axis of the throughbore defining the longitudinal direction of drilling.

2. The pin placement instrument according to claim 1, wherein the drill guide comprises two of said guide slot.

3. The pin placement instrument according to claim 2, wherein the two said guide slots are parallel to one another.

4. The pin placement instrument according to claim 1, wherein the at least one bushing has an abutment end for limiting movement in the longitudinal direction when placed in the at least one guide slot.

5. The pin placement instrument according to claim 1, further comprising a socket in the drill guide adapted to receive a handle for distal manipulation.

6. The pin placement instrument according to claim 1, further comprising one said pin for a set of one of the at least one guide slot and one of the at least one bushing, the one bushing being slidably engaged with the pin.

7. The pin placement instrument according to claim 1, wherein surfaces of the hook-like portion are generally transverse to the longitudinal direction.

8. The pin placement instrument according to claim 1, wherein the hook-like portion is complementary to a shape of at least one of the scapula head and glenoid neck.

9. The pin placement instrument according to claim 8, wherein the at least one guide slot is longitudinally aligned with at least one of a planned center of an implant, a location adjacent to the superior glenoid rim in alignment with the coracoid, and a base of the coracoid.

10. A pin placement instrument for placing at least one pin in a scapula comprising:

an anatomical interface with a hook-like portion being opened laterally relative to the instrument to receive a bone therein in a predetermined position, the hook-like portion having a first surface modeled specifically to match an upper surface of the scapula of a patient and a second surface modeled specifically to match an under surface of the scapula, the second surface opposite the first surface in a longitudinal direction of drilling, whereby the hook-like portion has a C-shape and is configured to hook onto both sides of a portion of the scapula;

a drill guide connected to the anatomical interface and defining at least one guide slot in the instrument and configured to be positioned on the upper surface of the scapula, the at least one guide slot having a lateral opening over its full length in the drill guide to allow lateral withdrawal of the instrument in a lateral direction from hooking engagement with the scapula when the at least one pin is placed in the scapula and is passing through the lateral opening; and at least one bushing removably placed in said at least one guide slot, the at least one bushing defining a throughbore aligned with the at least one guide slot and adapted to receive the at least one pin extending in the instrument when the at least one bushing is in the at least one guide slot for pin placement, the at least one bushing having an axis of the throughbore defining the longitudinal direction of drilling.

11. The pin placement instrument according to claim 10, wherein the drill guide comprises two of said guide slot.

12. The pin placement instrument according to claim 11, wherein the two said guide slots are parallel to one another.

13. The pin placement instrument according to claim 10, wherein the at least one bushing has an abutment end for limiting movement in the longitudinal direction when placed in the at least one guide slot.

14. The pin placement instrument according to claim 10, further comprising a socket in the drill guide adapted to receive a handle for distal manipulation.

15. The pin placement instrument according to claim 10, further comprising one said pin for a set of one of the at least one guide slot and one of the at least one bushing, the one bushing being slidably engaged with the pin.

16. The pin placement instrument according to claim 10, wherein surfaces of the hook-like portion are generally transverse to the longitudinal direction.

17. The pin placement instrument according to claim 10, wherein the hook-like portion is complementary to a shape of at least one of the scapula head and glenoid neck.

18. The pin placement instrument according to claim 17, wherein the at least one guide slot is longitudinally aligned with at least one of a planned center of an implant, a location adjacent to the superior glenoid rim in alignment with the coracoid, and a base of the coracoid.

19. A pin placement instrument for placing at least one pin in a scapula comprising:

an anatomical interface with a hook-like portion being opened laterally relative to the instrument to receive a bone therein in a predetermined position, the hook-like portion having a first surface modeled specifically to match an upper surface of the scapula of a patient and a second surface modeled specifically to match an under surface of the scapula, the second surface opposite the first surface in a longitudinal direction of drilling whereby the hook-like portion has a C-shape and is configured to hook onto both sides of a portion of the scapula;

a drill guide connected to the anatomical interface and defining at least one guide slot in the instrument and configured to be positioned on the upper surface of the scapula, the at least one guide slot having a lateral opening over its full length in the drill guide to allow lateral withdrawal of the instrument in a lateral direction from hooking engagement with the scapula when the at least one pin is placed in the scapula and is passing through the lateral opening; and at least one bushing removably placed in said guide slot, the bushing defining a throughbore aligned with the guide slot and adapted to receive the at least one pin extending longitudinally in the instrument when the bushing is in the guide slot for pin placement.

20. The pin placement instrument according to claim 19, wherein the drill guide comprises two of said guide slot.

21. The pin placement instrument according to claim 20, wherein the two said guide slots are parallel to one another.

22. The pin placement instrument according to claim 19, wherein the at least one bushing has an abutment end for limiting movement in the longitudinal direction when placed in the guide slot.

23. The pin placement instrument according to claim 19, further comprising a socket in the drill guide adapted to receive a handle for distal manipulation.

24. The pin placement instrument according to claim 19, further comprising one said pin for a set of one of the at least one guide slot and one of the at least one bushing, the one bushing being slidably engaged with the pin.

25. The pin placement instrument according to claim 19, wherein surfaces of the hook-like portion are generally transverse to the longitudinal direction.

26. The pin placement instrument according to claim 19, wherein the hook-like portion is complementary to a shape of at least one of the scapula head and glenoid neck.

27. The pin placement instrument according to claim 26, wherein the at least one guide slot is longitudinally aligned with at least one of a planned center of an implant, a location adjacent to the superior glenoid rim in alignment with the coracoid, and a base of the coracoid.

* * * * *